(12) United States Patent
Alken et al.

(10) Patent No.: US 7,307,091 B2
(45) Date of Patent: Dec. 11, 2007

(54) DEUTERATED 3-PIPERIDINOPROPIOPHENONE AND MEDICAMENTS CONTAINING SAID COMPOUNDS

(75) Inventors: Rudolf-Gisbert Alken, Zepernick (DE); Thomas Stabingis, Berlin (DE)

(73) Assignee: BDD Berolina Drug Development GmbH, Neuenhagen (DE)

( * ) Notice: Subject to any disclaimer, the term of this patent is extended or adjusted under 35 U.S.C. 154(b) by 570 days.

(21) Appl. No.: 10/476,743

(22) PCT Filed: Apr. 29, 2002

(86) PCT No.: PCT/DE02/01607

§ 371 (c)(1), (2), (4) Date: May 7, 2004

(87) PCT Pub. No.: WO02/088100

PCT Pub. Date: Nov. 7, 2002

(65) Prior Publication Data

US 2004/0186136 A1    Sep. 23, 2004

(30) Foreign Application Priority Data

May 2, 2001    (DE) ................................ 101 23 129

(51) Int. Cl.
*A61K 31/4515* (2006.01)
*C07D 211/32* (2006.01)

(52) U.S. Cl. ...................................... 514/317; 546/237

(58) Field of Classification Search ................ 546/237; 514/317

See application file for complete search history.

(56) References Cited

U.S. PATENT DOCUMENTS 3,995,047 A    11/1976    Morita et al.
4,638,009 A    1/1987    Itho et al.

FOREIGN PATENT DOCUMENTS

DE    24 58 638 A1    6/1975

OTHER PUBLICATIONS

Miyazaki et al, Kagaku no Ryoiki, Zokan, vol. 107, p. 133-137 (1975).*
Axel Dietrich, "Tolperison: Alter Wirkstoff oder neue Leitstruktur" 1999, Dissertation, Paderborn XP002232677.

* cited by examiner

*Primary Examiner*—Bernard Dentz
(74) *Attorney, Agent, or Firm*—Kriegsman & Kriegsman

(57) ABSTRACT

The invention discloses deuterated 3-piperidinopropiophenones as well as their physiologically tolerated salts. Furthermore, the invention concerns the use of deuterated 3-piperidinopropiophenones for the treatment of muscular illnesses as well as for the preparation of pharmaceutical drugs for the treatment of muscular illnesses.

In addition, the invention discloses pharmaceutical formulations containing deuterated 3-piperidinopropiophenones as well as their physiologically tolerated salts for the treatment of muscular illnesses in addition to containing pharmaceutically tolerated adjuvants and/or additives.

6 Claims, 3 Drawing Sheets

DEUTERATED 3-PIPERIDINOPROPIOPHENONE AND MEDICAMENTS CONTAINING SAID COMPOUNDS

The invention concerns deuterated 3-piperidinopropiophenones and their physiologically tolerated salts as well as pharmaceutical drugs containing these compounds.

Known representatives of 3-piperidinopropiophenones are tolperisone and eperisone (U.S. Pat. No. 3,995,047, U.S. Pat. No. 4,638,009). These compounds are used as spasmolytics and vasodilators.

The problem of the present invention is to make available 3-piperidinopropiophenones that, in comparison to the already known compounds, have improved pharmacokinetic and/or pharmacodynamic properties.

Surprisingly, it has now been found that the deuterated 3-piperidinopropiophenones in accordance with the invention have appreciably better pharmacokinetic and/or pharmacodynamic properties than the undeuterated compounds.

Thus, in accordance with the invention, the problem is solved by making available deuterated 3-piperidinopropiophenones of the general formula I,

[Formula (I)]

wherein

R represents an undeuterated, a mono- or polydeuterated, or a perdeuterated alkyl group containing up to 3 C atoms, the groups R' are all hydrogen or, in common, all represent deuterium, the groups R'' are, independently of one another, deuterium or hydrogen, and wherein at least one of the groups R, R', or R'' is deuterium or contains deuterium, as well as their physiologically tolerated salts.

Preferred are the following deuterated 3-piperidinopropiophenones in accordance with the invention:

4'-deuteromethyl-2-methyl-3-piperidinopropiophenone,

4'-methyl-2',3',5',6'-tetradeutero-2-methyl-3-piperidinopropiophenone,

4'-ethyl-2',3',5',6'-tetradeutero-2-methyl-3-piperidinopropiophenone,

4'-isopropyl-2',3',5',6'-tetradeutero-2-methyl-3-piperidinopropiophenone,

4'-n-propyl-2',3',5',6'-tetradeutero-2-methyl-3-piperidinopropiophenone,

4'-trideuteromethyl-2',3',5',6'-tetradeutero-2-methyl-3-piperidinopropiophenone, 4'-methyl-2-deuteromethyl-2-deuterium-3-piperidinopropiophenone, 4'-methyl-2-deuteromethyl-2-deuterium-3, 3-dideutero-3-piperidinopropiophenone, and 4'-trideuteromethyl-2',3',5',6'-tetradeutero-2-methyl-3,3-dideutero-3-piperidinopropiophenone.

Preferred is the use of the deuterated 3-piperidinopropiophenones in accordance with the invention as well as their physiologically tolerated salts for the treatment of illnesses with symptoms in the muscular region.

Especially preferred is the use of deuterated 3-piperidinopropiophenones as well as their physiologically tolerated salts for the preparation of pharmaceutical drugs for the treatment of illnesses with symptoms in the muscular region.

Especially preferred are pharmaceutical formulations that contain the deuterated 3-piperidinopropiophenones in accordance with the invention as well as their physiologically tolerated salts for the treatment of illnesses with symptoms in the muscular region in addition to containing pharmaceutically tolerated adjuvants and/or additives.

The preparation of the deuterated tolperisone that is used in accordance with the invention is in itself known. The deuterated propiophenones employed as starting compound were prepared using deuterated toluene derivatives by Friedel-Crafts acylation with propionyl chloride (Organikum, 15th edition, 1977, pp. 404-405). Used in this process were the commercially obtainable toluene derivatives trideuteromethylbenzene and perdeuterotoluene and the known 2,3,4,5,6-pentadeuterotoluene (A. Borovik et al., Angew. Chem., Int. Ed., 2000, 39(22), 4117-4118).

The reaction to give the deuterated tolperisone derivatives can take place in analogy to the known syntheses for 3H-tolperisone (Dietrich, A.; Fels, G.; J. Labelled Compd. Radiopharm. (1999), 42(12), 1125-1134, as well as Dietrich, A.; Dissertation 1999, Univ.-GH Paderborn).

In this work, A. Dietrich describes, among other things, the synthesis of tolperisone derivatives that are tritiated and deuterated in the 3' position and in the 3',5' position. These substances were used for the investigation of the mode of action and pharmacology of tolperisone.

The tolperisone derivatives that are deuterated in the 2 position and in the 2-methyl position were produced, starting from the known 2,3-didehydrotolperisone (Dietrich, A., Dissertation 1999, Univ.-GH Paderborn), by reaction with deuterium. The compounds that are deuterated in the 1 position were obtained in a way that is in itself known by the use of deuterated paraformaldehyde in the Mannich reaction with the corresponding propiophenone derivatives.

Conventional physiologically tolerated inorganic and organic acids are, for example, hydrochloric acid, hydrobromic acid, phosphoric acid, sulfuric acid, oxalic acid, maleic acid, fumaric acid, lactic acid, tartaric acid, malic acid, citric acid, salicylic acid, adipic acid, and benzoic acid. Further salts that can be used are described, for example, in Fortschritte der Arzneimittelforschung [Progress in Drug Research], Vol. 10, pages 224-225, Birkhäuser Publishers, Basel and Stuttgart, 1966, and Journal of Pharmaceutical Sciences, Vol. 66, pages 1-5 (1977).

The acid addition salts are obtained, as a rule, in a way that is in itself known by mixing the free base or solutions thereof with the corresponding acid or solutions thereof in an organic solvent, such as, for example, in a lower alcohol, such as methanol, ethanol, n-propanol, or isopropanol, or in a lower ketone, such as acetone, methyl ethyl ketone, or methyl isobutyl ketone, or in an ether, such as diethyl ether, tetrahydrofuran, or dioxane. In order to achieve better separation of the crystals, it is also possible to use mixtures of the solvents mentioned. Beyond this, it is possible to prepare physiologically tolerated aqueous solutions of acid addition salts of the compounds used in accordance with the invention in an aqueous acid solution.

The acid addition salts of the compounds in accordance with the invention can be transformed into the free base in ways that are in themselves known—for example, with alkalis or ion exchangers. Additional salts can be obtained from the free base by reaction with inorganic or organic acids, in particular with those suitable for the formation of salts that can be used therapeutically. These or else other salts of the new compound, such as, for example, the picrate, can also serve for the purification of the free base by transforming the free base into a salt, separating the latter, and liberating the base once again from the salt.

The subject of the present invention is also pharmaceutical drugs for oral, rectal, topical (cutaneous, transdermal, local), subcutaneous, intravenous, or intramuscular application that, in addition to conventional carriers and diluents, contain a compound of the general formula I or its acid addition salt as the active ingredient.

The pharmaceutical drugs of the invention are prepared in a known way in a suitable dosage with the conventional solid or liquid carriers or diluents and the conventionally used technical pharmaceutical adjuvants depending on the desired kind of application. The preferred formulations consist of a form of administration that is suitable for oral application. Such forms of administration are, for example, tablets, film tablets, dragées, capsules, pills, powders, solutions, or suspensions or depot forms.

The topical application can take place, for example, in the form of salves, creams, gels, solutions, or bandages.

Obviously, parenteral formulations, such as injection solutions, also come into consideration. Furthermore, suppositories are also mentioned as formulations by way of example.

Corresponding tablets can, for example, be obtained by mixing the active ingredient with known adjuvants, such as, for example, inert diluents, such as dextrose, sugar, sorbitol, mannitol, polyvinyl pyrrolidone, disintegrators, such as cornstarch or alginic acid, binders, such as starches or gelatins, lubricants, such as magnesium stearate or talc, and/or means for achieving a depot effect, such as carboxylpolymethylene, carboxylmethylcellulose, cellulose acetate phthalate, or polyvinyl acetate. The tablets can also consist of several layers.

In a corresponding manner, dragées can be prepared by coating cores, prepared in analogy to the tablets, with substances usually used in dragée coats, such as, for example, polyvinyl pyrrolidone or shellac, gum arabic, talc, titanium dioxide, or sugar. Here, the dragée shell can also consist of several layers, wherein the adjuvants mentioned above for the tablets can be used.

Solutions or suspensions containing the active ingredient used in accordance with the invention can contain, in addition, substances that improve taste, such as saccharin, cyclamate, or sugar, as well as, for example, flavoring substances, such as vanilla or orange extract. In addition, they can contain suspending agents, such as sodium carboxymethylcellulose, or preservatives, such as p-hydroxybenzoates. For example, capsules that contain active ingredients can be prepared by mixing the active ingredient with an inert carrier, such as lactose or sorbitol, followed by encapsulation in gelatin capsules.

Suitable suppositories can be prepared, for example, by admixture with carriers, such as neutral fats or polyethylene glycol or their derivatives, which are provided for this purpose.

The preparation of the pharmaceutical drug in accordance with the invention for topical application is known to the person skilled in the art. In the preparation of the pharmaceutical drug in accordance with the invention for transdermal application, the adjuvants and enhancers that are in themselves known are used.

The preparation of the pharmaceutical formulations in accordance with the invention is in itself known and is described in handbooks known to the person skilled in the art, such as, for example Hager's Handbuch [Hager's Handbook] (5th) 2, 622-1045; List et al., Arzneiformenlehre [Drug Forms], Stuttgart: Wiss. Pub. Co. 1985; Sucker et al., Pharmazeutische Technologie [Pharmaceutical Technology], Stuttgart: Thieme 1991; Ullmann's Enzyklopädie [Ullmann's Encyclopedia] (5th) A 19, 241-271; Voigt, Pharmazeutische Technologie [Pharmaceutical Technology], Berlin: Ullstein Mosby 1995.

The pharmaceutical drugs prepared in this way can be used for the treatment of illnesses with symptoms in the muscular region.

The compounds in accordance with the invention have a number of advantages in comparison with the compounds known in the prior art, which do not bear any deuterium. The deuteration brings about a change in metabolism in the organism. In particular, the hydroxylation on the phenyl group is impeded, this leading to a reduced first-pass effect. In this way it is possible to change the dosage and to create longer-acting formulations, which, in the form of depot formulations, can also improve compliance.

In addition, the pharmacodynamics are also changed, because the deuterated compounds form completely different hydrate shells, so that the distribution in the organism differs markedly from that of the undeuterated compounds.

The metabolism of tolperisone and of substances derived therefrom occurs primarily in the liver, this resulting in the observation of a strong first-pass effect. Only one-fifth of the administered dose is once again found unchanged in the blood.

Decisive for the hepatic metabolism of medications and xenobiotics are cytochrome P450 (CYP) enzymes. The primary metabolites during hepatic degradation are formed by hydroxylation of the alkyl substituents located on the aromatic ring and by hydroxylation of the aromatic rings themselves (Miyazaki, Ishibashi Takayama; 4th symposium on Drug Metabolism and Action, 1972, Sendai; Japan: 154-164).

In order to obtain more detailed knowledge regarding the hepatic metabolism of tolperisone and of the claimed deuterated analogs, pharmacokinetic in-vitro studies were carried out with the cytochrome P450 families (CYP1A1, CYP1A2, CYP2C8, CYP2C19, CYP2D6, CYP2E1, CYP3A4) that are known to the person of average skill in the art and are most commonly encountered in the liver.

The results of these investigations are presented in FIGS. 1 to 3.

Shown therein are the following:

FIG. 1 shows the different decreases in tolperisone concentration due to enzymatic degradation by cytochrome oxidases over time.

In accordance therewith, tolperisone is transformed above all by CYP2C19 and CYP2D6. The other cytochromes investigated contribute at most insignificantly to the biological degradation of tolperisone.

Figure 1:
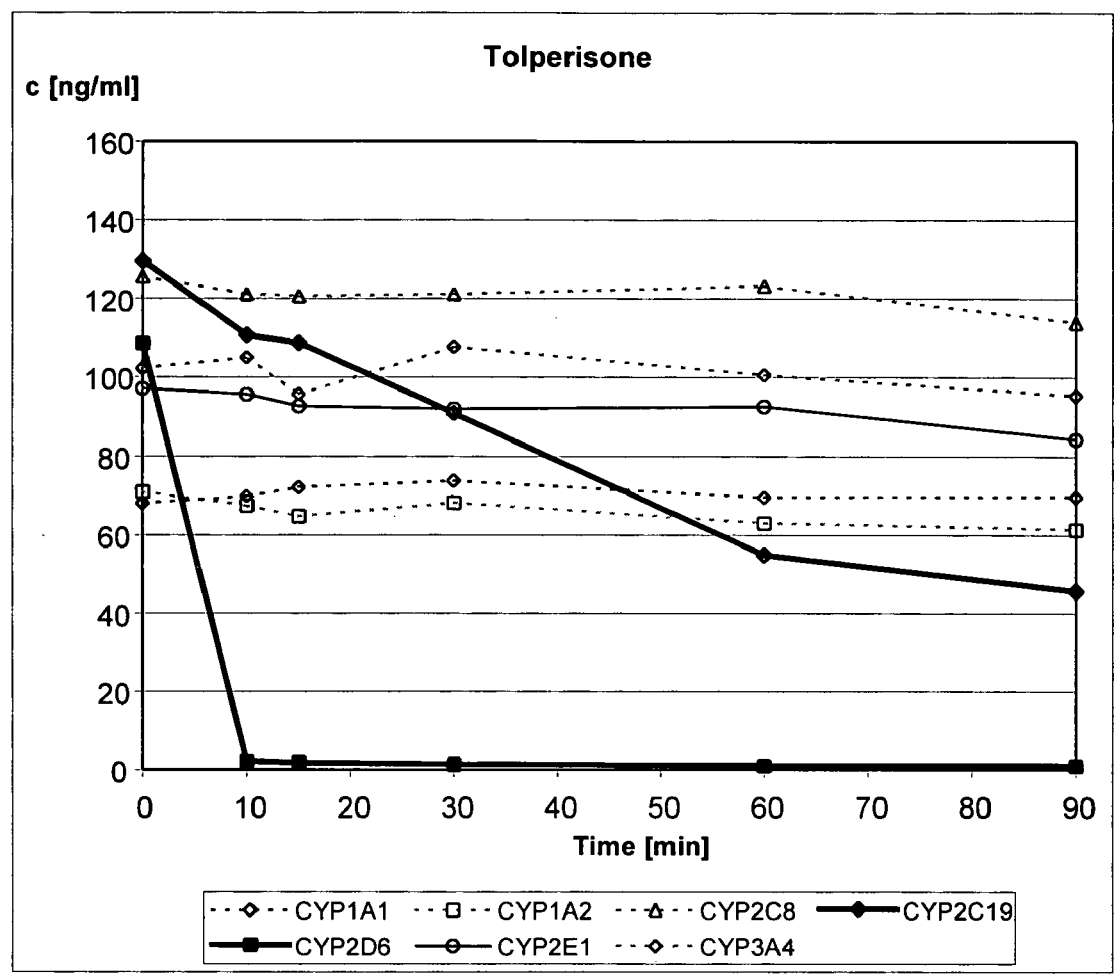
FIG. 1 shows the enzymatic degradation of tolperisone by cytochrome oxidases.
Figure 2:
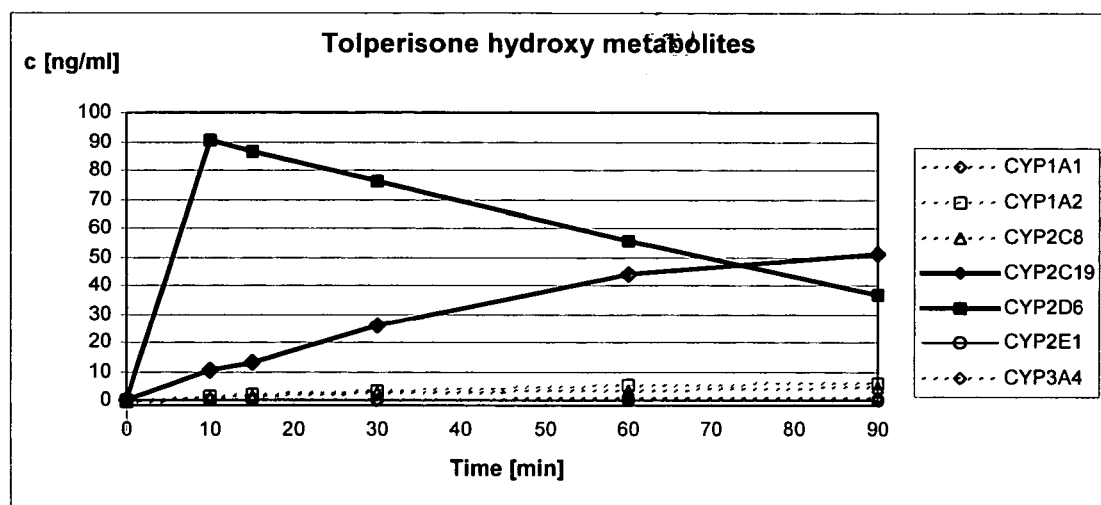
FIG. 2 shows the formation of hydroxy metabolites from tolperisone by CYP2D6 and CYP2C19 in comparison to less active cytochromes.

The primary metabolites that are formed by hydroxylation are formed by CYP2C19 and CYP2D6 to the same extent as the substrate is degraded (see FIG. 2).

Surprisingly, the hepatic metabolism of the deuterated compounds in accordance with the invention by cytochrome P450 oxidases differs markedly from that of the corresponding undeuterated substances.

Figure 3:
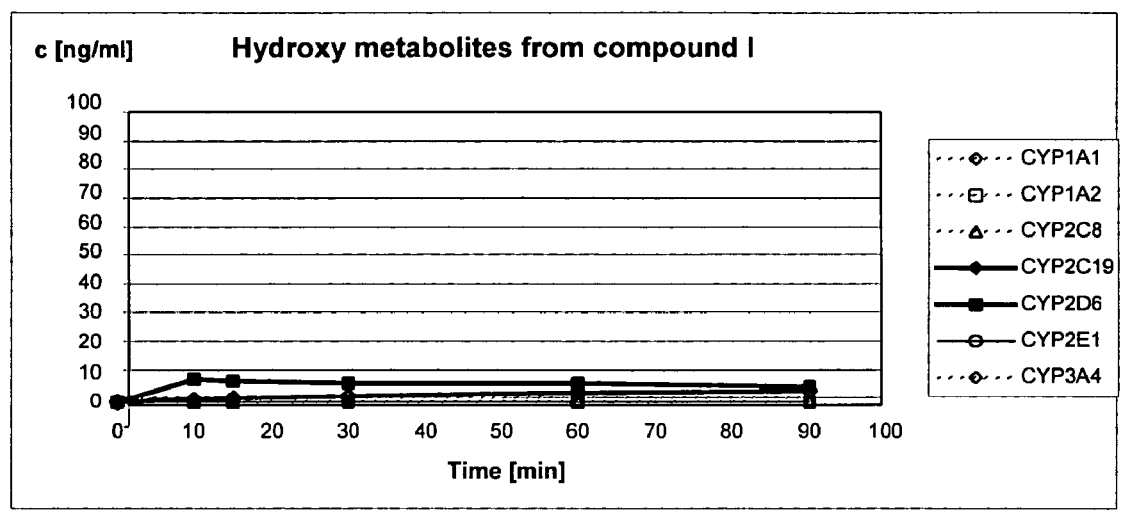
FIG. 3 shows the formation of hydroxy metabolites from compound I by cytochrome P450 enzymes.

For example, the enzymatic hydroxylation of 1-[4-(trideuteromethyl)tetradeuterophenyl]-2-methyl-3-piperidin-1-yl-1-propanone (I; formula I with R=$CD_3$, R'=D, R''=H) by CYP2C19 and CYP2D6 is effectively retarded by a factor of 10 in comparison to that of tolperisone (see FIG. 3).

This results in an improvement in the effectiveness, because it is compelling to assume a prolongation in the duration of action. The therapeutic benefit lies in a reduction in dose when pharmaceutical drugs prepared from the deuterated propiophenones in accordance with the invention are used in comparison to the previously used non-deuterated analogous compounds.

Accordingly, it is possible to develop completely novel formulation forms.

The following examples illustrate the invention:

EXAMPLE 1

Preparation of 4'-trideuteromethylpropiophenone

In a three-neck flask equipped with a stirrer, a dropping funnel, and a reflux condenser with a calcium chloride drying tube, 40 mL of dichloroethane were treated with 16 mg of anhydrous, finely powdered aluminum chloride. Under ice cooling, 13.88 g of propionyl chloride were added dropwise. Then, 9.5 g of trideuteromethylbenzene (toluene-d3) were added dropwise at such a rate that the temperature of the reaction solution was kept constant at 20° C. After the addition had ended, the mixture was stirred for 2 hours and subsequently allowed to stand overnight. The ketone-aluminum chloride complex that formed was decomposed by pouring the reaction mixture carefully onto 50 mL of ice. The organic phase was separated off and the aqueous phase was extracted three times with dichloroethane. The combined organic extracts were washed with water, 2% aqueous sodium hydroxide solution, and once again with water and then dried over potassium carbonate.

The solvent was removed and the residue was distilled in vacuum. Yield: 10.2 g (68%) of 4'-trideuteromethypropiophenone as a colorless liquid.

$C_{10}H_9D_3O$: 151.223

Calcd. C 79.43 H 9.99

Found C 79.41 H 10.01

$^1$H-NMR: In comparison to the $^1$H-NMR spectrum of the non-deuterated 4'-methylpropiophenone, it was possible to establish the absence of the resonance signal of the aromatic $CH_3$ group in the $^1$H-NMR spectrum of the product, the spectra being otherwise in agreement.

EXAMPLE 2

Preparation of 4'-trideuteromethyl-2',3',5',6'-tetradeuteropropiophenone In analogy to Example 1, 16 g of anhydrous, finely powdered aluminum chloride in 40 mL of dichloroethane were treated under ice cooling with 13.88 g of propionyl chloride and brought to reaction with 10.02 g of trideuteromethyl-2,3,4,5,6-tetradeuterobenzene [toluene-d8].

In this case, however, the ketone-aluminum chloride complex was decomposed by pouring the reaction mixture into ice-cooled $D_2O$. The further workup was conducted in analogy to Example 1.

Yield: 10.24 g (66%) of 4'-trideuteromethyl-2',3',5',6'-tetradeuterophenylpropiophenone* as a colorless liquid.

*Presumably, "4'-trideuteromethyl-2',3',5',6'-tetradeuteropropiophenone" is meant.—Translator's Note.

$C_{10}H_5D_7O$:

Calcd. C 77.37 H 12.33

Found C 77.40 H 12.31

$^1$H-NMR: In comparison to the $^1$H-NMR spectrum of the non-deuterated 4'-methylpropiophenone, it was possible to establish the absence of the resonance signal of the aromatic $CH_3$ group as well of the aromatic protons in the $^1$H-NMR spectrum of the product, the spectra being otherwise in agreement.

EXAMPLE 3

Preparation of 4'-methyl-2',3',5',6'-tetradeuteropropiophenone In analogy to Example 2, 16 g of anhydrous, finely powdered aluminum chloride in 40 mL of dichloroethane were treated under ice cooling with 13.88 g of propionyl chloride and brought to reaction with 9.72 g of 2,3,4,5,6-pentadeuterotoluene [toluene-d5]. The workup took place as described in Example 1.

Yield: 9.59 g (63%) of 4'-methyl-2',3',5',6'-tetradeuteropropiophenone as a colorless liquid.

$C_{10}H_8D_4O$:

Calcd. C 78.9 H 10.59

Found C 79.3 H 10.53

$^1$H-NMR: In comparison to the $^1$H-NMR spectrum of the non-deuterated 4'-methylpropiophenone, it was possible to establish the absence of the resonance signal of the aromatic protons in the $^1$H-NMR spectrum of the product, the spectra being otherwise in agreement.

EXAMPLE 4

Preparation of 4'-trideuteromethyl-2-methyl-3-piperidinopropiophenone 1.15 g of 4'-trideuteromethylpropiophenone were dissolved in 5 mL of methanol and subsequently 0.3 g of paraformaldehyde and 1.1 g of piperidine hydrochloride were added under stirring. The reaction mixture was heated to reflux until the end point of the reaction was reached (solidification of the reaction mixture). Subsequently, 10 mL of chloroform were added, the organic phases were dried over sodium sulfate and filtered, and the solvent was removed in vacuum. The obtained solid was finely pulverized and washed with acetone. The 1.5 g of the crystalline crude product obtained was converted into the hydrochloride, which was recrystallized from methanol.

Yield: 1.45 g (73%) in the form of needles.

Melting point: 167-169° C.

$^1$H-NMR (200 MHz, $CDCl_3$): δ=1.18 (d, 3H, $CH_3$), 1.25-1.68 (m, 6H, 3×$CH_2$), 2.18-2.45 (m, 4H, 2×$CH_2$), 2.35 and 2.65 (d and AB spectrum, J=7.1 Hz, $J_{A,B}$=12.4 Hz, 2H, $CH_2$), 3.69 (m, 1H, CH), 7.78 (s, 4H, Ar—H).

$^{13}$C-NMR (50 MHz, $CDCl_3$): δ=18.00 (Ar—$CD_3$), 20.01 ($CH_3$), 22.15 ($CH_2$), 23.15 ($CH_2$), 34.25 (CH), 52.67 (2 $CH_2$), 58.53 ($CH_2$), 126.73 ($C_{arom}$), 129.42 ($C_{arom}$), 131.34 ($C_{arom}$), 155.02 ($C_{arom}$), 204.02 (C:O).

$C_{16}H_{20}NOD_3 \cdot HCl$ (284.85):

Calcd. C 67.47 H 9.55 N 4.92

Found C 67.45 H 9.56 N 4.91

EXAMPLE 5

Preparation of 4'-methyl-2',3',5',6'-tetradeutero-2-methyl-3-piperidinopropiophenone In analogy to Example 4, 1.16 g of 4'-methyl-2',3',5',6'-tetradeuteropropiophenone were dissolved in 5 mL of methanol and subsequently brought to reaction with 0.3 g of paraformaldehyde and 1.1 g of piperidine hydrochloride. The product was isolated as the hydrochloride.

Yield: 1.42 g (71%) in the form of needles.
Melting point: 174-176° C.
$^1$H-NMR (200 MHz, CDCl$_3$): δ=1.18 (d, 3H, CH$_3$), 1.25-1.68 (m, 6H, 3 CH$_2$), 2.18-2.45 (m, 4H, 2 CH$_2$), 2.35 and 2.65 (d and AB spectrum, J=7.1 Hz, J$_{A,B}$=12.4 Hz, 2H, CH$_2$), 2.41 (s, 3H, Ar—CH$_3$), 3.69 (m, 1H, CH).
C$_{16}$H$_{19}$NOD$_4$ HCl (285.85)
Calcd. C 67.23 H 9.87 N 4.9
Found C 67.21 H 9.89 N 4.8

EXAMPLE 6

Preparation of 4'-trideuteromethyl-2',3',5',6'-tetradeutero-2-methyl-3-piperidinopropiophenone In analogy to Example 4, 1.09 g of 4'-trideuteromethyl-2',3',5',6'-tetradeuteropropiophenone were dissolved in 5 mL of methanol and subsequently brought to reaction with 0.3 g of paraformaldehyde and 1.1 g of piperidine hydrochloride. The product was isolated as the hydrochloride.

Yield: 1.46 g (72%) in the form of needles. Melting point: 177-178° C.
C$_{16}$H$_{16}$NOD$_7$ · HCl (288.87)
Calcd. C 66.53 H 10.81 N 4.85
Found C 66.55 H 10.84 N 4.87
$^1$H-NMR (200 MHz, CDCl$_3$): δ=1.18 (d, 3H, CH$_3$), 1.25-1.68 (m, 6H, 3 CH$_2$), 2.18-2.45 (m, 4H, 2 CH$_2$), 2.35 and 2.65 (d and AB spectrum, J=7.1 Hz, J$_{A,B}$=12.4 Hz, 2H, CH$_2$), 3.69 (m, 1H, CH).
IR: ν$_{max}$ (Nujol) 2721, 2639, 2532, 2408, 1674 (C:O), 1580 (Ar), 1544, 1460, 1411, 1378, 1331, 1298, 1244, 1211, 1159, 1121, 1083, 1081, 1021, 721, 638 cm$^{-1}$.

EXAMPLE 7

Preparation of 4'-methyl-2-deuteromethyl-2-deuterium-3-piperidinopropiophenone

To a solution of 10 g (41 mmol) of 2,3-didehydrotolperisone in 150 mL of ethyl acetate were added 100 mg of Pd/C (10%) and the reaction flask was flushed with deuterium gas and then joined to a Paar apparatus. The deuteration takes place at 2 atm at room temperature overnight. The reaction mixture was filtered off over Celite and the filtrate was concentrated in vacuum. Subsequently, the residue was taken up in 1N NaOH and extracted with diethyl ether and the organic phase was separated off, dried over sodium sulfate, filtered, and concentrated in vacuum. The resulting amine was dissolved in diethyl ether and acetyl chloride and methanol were added in order to prepare the hydrochloride.

Yield: 8.6 g (85%) of the deuterated tolperisone were obtained.
Melting point: 178° C.
$^1$H-NMR (200 MHz, CDCl$_3$): δ=1.15 (d, 2H, CDH$_2$), 1.30-1.72 (m, 6H, 3 CH$_2$), 2.20-2.48 (m, 4H, 2 CH$_2$), 2.48 (s, 3H, CH$_3$), 2.49 and 2.85 (d and AB spectrum, J=7.2 Hz, J$_{A,B}$=12.6 Hz, 2H, CH$_2$), 7.95 (s, 2H, AR—H).
$^{13}$C-NMR (50 MHz, CDCl$_3$): δ=19.21 (Ar—CH$_3$), 18.78 (CDH$_2$), 22.20 (CH$_2$), 22.95 (CH$_2$), 35.32 (CD), 52.53 (2 CH$_2$), 58.60 (CH$_2$), 129.33 (C$_{arom}$), 130.32 (C$_{arom}$), 132.15 (C$_{arom}$), 145.55 (s, C$_{arom}$), 201.02 (C:O).
C$_{16}$H$_{21}$NOD$_2$ HCl (283.48):
Calcd. C 67.71 H 9.23 N 4.93
Found C 67.73 H 9.21 N 4.95

EXAMPLE 8

In-vitro experiments on biological degradation of test substances by cytochrome P450 enzymes Cell lines used: CYP1A1, CYP1A2, CYP2C8, CYP2C19, CYP2D6, CYP2E1, CYP3A4.

Incubation at 37° C. in 200 μL of incubation solution consisting of 0.1M potassium phosphate or 0.5M Tris HCl buffer (pH 7.4), 3 mM NADPH with a protein concentration of 0.5 mg/mL.

The analysis of the enzyme test was conducted by means of LC/MS/MS.

What is claimed is:

1. A deuterated 3-piperidinopropiophenone of the general formula I,

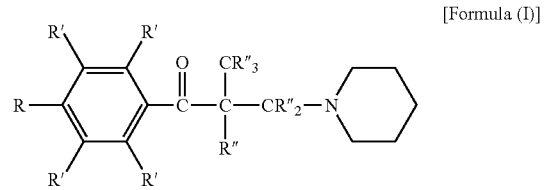

[Formula (I)]

wherein

R represents an undeuterated, a mono- or polydeuterated, or a perdeuterated alkyl group containing up to 3 C atoms, the groups R' are all hydrogen or all represent deuterium, the groups R" are, independently of one another, deuterium or hydrogen, and wherein at least one of the groups R, R', or R" is deuterium or contains deuterium, as well as their physiologically tolerated salts.

2. The deuterated 3-piperidinooropiophenone according to claim 1, namely,

4'-trideuteromethyl-2-methyl-3-piperidinopropiophenone,

4'-methyl-2', 3', 5', 6'-tetradeutero-2-methyl-3-piperidinopropiophenone,

4'-ethyl-2', 3', 5', 6'-tetradeutero-2-methyl-3-piperidinopropiophenone,

4'-isopropyl-2', 3', 5', 6'-tetradeutero-2-methyl-3-piperidinopropiophenone,

4'-n-propyl-2', 3', 5', 6'-tetradeutero-2-methyl-3-piperidinopropiophenone,

4'-trideuteromethyl-2', 3', 5', 6'-tetradeutero-2-methyl-3-piperidinopropiophenone, 4'-methyl-2-deuteromethyl-2-deuterium -3-piperidinopropiophenone, 4'-methyl-2-deuteromethyl-2-deuterium-3,3-dideutero-3-piperidinopropiophenone, and 4'-trideuteromethyl-2', 3', 5', 6-tetradeutero-2-methyl-3,3-dideutero-3-piperidino-propiophenone.

3. A method of treating a patient in need of at least one of a spasmolytic and a vasodilator comprising administering to the patient an effective amount of the deuterated 3-piperidinopropiophenone according to claim 1 or 2 or its physiologically tolerated salts.

4. A method of making a pharmaceutical drug, said method comprising the steps of providing the deuterated 3-piperidinopropiophenone according to claim 1 or 2 or its physiologically tolerated salts and mixing said deuterated 3-piperidinopropiophenone or its physiologically tolerated salts with a suitable vehicle.

5. Pharmaceutical formulation containing the deuterated 3-piperidinopropiophenone according to claim 1 or 2 or its physiologically tolerated salts in addition to pharmaceutically tolerated adjuvants and/or additives.

6. The deuterated 3-piperidinopropiophenone according to claim 1 or 2 in substantially isolated form.

* * * * *